United States Patent
McCord et al.

(10) Patent No.: US 10,619,218 B2
(45) Date of Patent: *Apr. 14, 2020

(54) MATERIALS AND METHODS FOR DETECTING SOURCE BODY FLUIDS

(71) Applicants: Bruce McCord, Miami, FL (US);
Joana Antunes, Miami, FL (US)

(72) Inventors: Bruce McCord, Miami, FL (US);
Joana Antunes, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 16 days.

This patent is subject to a terminal disclaimer.

(21) Appl. No.: 16/054,210

(22) Filed: Aug. 3, 2018

(65) Prior Publication Data
US 2019/0284643 A1 Sep. 19, 2019

Related U.S. Application Data

(62) Division of application No. 15/921,079, filed on Mar. 14, 2018, now Pat. No. 10,053,740.

(51) Int. Cl.
*C07H 21/04* (2006.01)
*C12Q 1/68* (2018.01)
*C12Q 1/6888* (2018.01)
*C12Q 1/6881* (2018.01)

(52) U.S. Cl.
CPC ......... *C12Q 1/6888* (2013.01); *C12Q 1/6881* (2013.01); *C12Q 2600/154* (2013.01)

(58) Field of Classification Search
None
See application file for complete search history.

(56) References Cited

PUBLICATIONS

Yoshino et al. (J. of Alzheimer's Disease, vol. 58, pp. 687-694, 2017) (Year: 2017).*
An, J. H. et al., "Body fluid identification in forensics." BMB Reports, Sep. 2012, 45 (10): 545-553.
Antunes, J. et al., "Forensic discrimination of vaginal epithelia by DNA methylation analysis through pyrosequencing." Electrophoresis, 2016, 37: 2751-2758.
Antunes, J. et al., "High-resolution melt analysis of DNA methylation to discriminate semen in biological stains." Analytical Biochemistry, 2016, 494: 40-45.
Antunes, J. et al., "Tissue-specific DNA methylation patterns in forensic samples detected by Pyrosequencing®." Pyrosequencing, Department of Chemistry and Biochemistry, Florida International University, School of Criminal Justice, the University of Southern Mississippi, 2014, 1-21.
Du, P. et al., "Comparison of Beta-value and M-value methods for quantifying methylation levels by microarray analysis." BMC Bioinformatics, 2010, 11 (587): 1-9.
Eads, C. A., Laird, P. W., "Combined Bisulfite Restriction Analysis (COBRA)." Methods in Molecular Biology, 2002, 200: 71-85.
Ehrich, M. et al., "Quantitative high-throughput analysis of DNA methylation patterns by base-specific cleavage and mass spectrometry." PNAS, Nov. 2005, 102 (44): 15785-15790.
Fraga, M. F. et al., "Epigenetic differences arise during the lifetime of monozygotic twins." PNAS, Jul. 2005, 102 (30): 10604-10609.
Gršković, B. et al., "DNA methylation: the future of crime scene investigation?" Mol. Biol. Rep., 2013, 40: 4349-4306.
Haas, C. et al., "mRNA profiling for the identification of blood—Results of a collaborative EDNAP exercise." Forensic Science International: Genetics, 2011, 5: 21-26.
Harbison, S. A., Fleming, R. I., "Forensic body fluid identification: state of the art." Research and Reports in Forensic Medical Science, 2016, 6: 11-23.
Juusola, J., Ballantyne, J., "mRNA Profiling for Body Fluid Identification by Multiplex Quantitative RT-PCR." J. Forensic. Sci., Nov. 2007, 52 (6): 1252-1262.
Li, L., Dahiya, R., "MethPrimer: designing primers for methylation PCRs." Bioinformatics, May 2002, 18 (11): 1427-1431.
Park, J. et al., "Identification of body fluid-specific DNA methylation markers for use in forensic science." Forensic Science International: Genetics, 2014, 13: 147-153.
Paul, C. L., Clark, S. J., "Cytosine Methylation: Quantitation by Automated Genomic Sequencing and GENESCAN Analysis." BioTechniques, Jul. 1996, 21 (1): 126-133.
Tost, J., Gut, I. G., "Analysis of Gene-Specific DNA Methylation Patterns by Pyrosequencing® Technology." Methods in Molecular Biology, 2007, 373: 89-102.
Tusnády, G. E. et al., "BiSearch: primer-design and search tool for PCR on bisulfite-treated genomes." Nucleic Acids Research, 2005, 33 (1): 1-6.

(Continued)

*Primary Examiner* — Jeanine A Goldberg
(74) *Attorney, Agent, or Firm* — Saliwanchik, Lloyd & Eisenschenk

(57) ABSTRACT

The invention pertains to analyzing the levels of DNA methylation at specific genetic loci to detect specific body fluids, for example, vaginal secretions or vaginal epithelial cells, semen or sperms, saliva or buccal epithelial cells, or blood or blood cells. Particularly, the levels of methylation of DNA at the genetic loci corresponding to SEQ ID NOs: 1, 6, 11, and 16 are used to detect vaginal secretions or vaginal epithelial cells, semen or sperms, saliva or buccal epithelial cells, and blood or blood cells, respectively. The level of methylation at the specific loci can be determined by high-resolution melt analysis (HRM) or sequencing of the amplicons produced using specific primers designed to amplify the specific loci. Kits containing the primers and reagents for carrying out the methods disclosed herein are also provided.

10 Claims, 2 Drawing Sheets
(2 of 2 Drawing Sheet(s) Filed in Color)
Specification includes a Sequence Listing.

(56) References Cited

PUBLICATIONS

Warnecke, P. M. et al., "Identification and resolution of artifacts in bisulfite sequencing." Methods, 2002, 27: 101-107.
Xiong, Z., Laird, P. W., "COBRA: a sensitive and quantitative DNA methylation assay." Nucleic Acids Research, 1997, 25 (12): 2532-2534.

* cited by examiner

SEQUENCE LISTING

<160> NUMBER OF SEQ ID NOS: 20

<210> SEQ ID NO 1
<211> LENGTH: 131
<212> TYPE: DNA
<213> ORGANISM: Homo sapiens

<400> SEQUENCE: 1
tcaaatcagg gtgtgggcag agctgtgctc cctctggacg ccttttccct cttccagcat    60
ctgttggctg ctggcgcccc ttggcacgtg gtgcatcgct ccagtctggg ctctgtcttc    120
ctggcatgct c                                                         131

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ttaaattagg gtgtgggtag a                                              21

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
aaacatacca aaaaacaaa ac                                              22

<210> SEQ ID NO 4
<211> LENGTH: 131
<212> TYPE: DNA
<213> ORGANISM: Artificial Sequence
<220> FEATURE:
<223> OTHER INFORMATION: Sequence of the locus specific for vaginal
      epithelial cell after bisulfite treatment assuming 100%
      unmethylation of all CpG sites

<400> SEQUENCE: 4
ttaaattagg gtgtgggtag agttgtgttt tttttggatg tttttttttt ttttagtat    60

```
ttgttggttg ttggtgtttt ttggtatgtg gtgtattgtt ttagtttggg ttttgttttt    120
ttggtatgtt t                                                          131

<210> SEQ ID NO 5
<211> LENGTH: 131
<212> TYPE: DNA
<213> ORGANISM: Homo sapiens

<400> SEQUENCE: 5
tcaaatcagg gtgtgggcag agctgtgctc cctctggacg ccttttccct cttccagcat    60
ctgttggctg ctggcgcccc ttggcacgtg gtgcatcgct ccagtctggg ctctgtcttc    120
ctggcatgct c                                                         131

<210> SEQ ID NO 6
<211> LENGTH: 91
<212> TYPE: DNA
<213> ORGANISM: Homo sapiens

<400> SEQUENCE: 6
gggtgagggc caagggcac cgcccctgag aaccaccccc aacgcgaggc cacccgcttc    60
ccgggccggt cagatgaggt tttgagggga g                                    91

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
gggtgagggt ttaagggt                                                   18

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ctcccctcaa aacctcat                                                   18

<210> SEQ ID NO 9
<211> LENGTH: 91
<212> TYPE: DNA
<213> ORGANISM: Artificial Sequence
<220> FEATURE:
<223> OTHER INFORMATION: Sequence of the locus specific for sperm after
      bisulfite treatment assuming 100% unmethylation of all CpG sites

<400> SEQUENCE: 9
gggtgagggt ttaagggtat tgtttttgag aattattttt aatgtgaggt tatttgtttt    60
ttgggttggt tagatgaggt tttgagggga g                                    91

<210> SEQ ID NO 10
<211> LENGTH: 91
<212> TYPE: DNA
<213> ORGANISM: Homo sapiens

<400> SEQUENCE: 10
gggtgagggc caagggcac cgcccctgag aaccaccccc aacgcgaggc cacccgcttc    60
```

```
ccgggccggt cagatgaggt tttgagggga g                               91
```

<210> SEQ ID NO 11
<211> LENGTH: 156
<212> TYPE: DNA
<213> ORGANISM: Homo sapiens

<400> SEQUENCE: 11

```
aaggagaggg ctggcaagag agccgcggca gccgtggcag ggtgtagggg acggtggacg   60
gccagggccc ccccctctct ctctttctct ctctctctct tgcttggttt ctgtaatgag  120
gaagttctcc gcagctcagt ttcctttccc tcactg                            156
```

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12

```
aaggagaggg ttggtaagag agt                                         23
```

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13

```
caataaaaaa aaaaaaacta aactacraaa aac                              33
```

<210> SEQ ID NO 14
<211> LENGTH: 156
<212> TYPE: DNA
<213> ORGANISM: Artificial Sequence
<220> FEATURE:
<223> OTHER INFORMATION: Sequence of the locus specific for blood cells
      after bisulfite treatment assuming 100% unmethylation of all CpG
      sites

<400> SEQUENCE: 14

```
aaggagaggg ttggtaagag agttgtggta gttgtggtag ggtgtagggg atggtggatg   60
gttagggttt ttttttttt ttttttttt ttttttttt tgtttggttt ttgtaatgag   120
gaagtttttt gtagtttagt ttttttttt ttattg                            156
```

<210> SEQ ID NO 15
<211> LENGTH: 156
<212> TYPE: DNA
<213> ORGANISM: Homo sapiens

<400> SEQUENCE: 15

```
aaggagaggg ctggcaagag agccgcggca gccgtggcag ggtgtagggg acggtggacg   60
gccagggccc ccccctctct ctctttctct ctctctctct tgcttggttt ctgtaatgag  120
gaagttctcc gcagctcagt ttcctttccc tcactg                            156
```

<210> SEQ ID NO 16
<211> LENGTH: 199
<212> TYPE: DNA
<213> ORGANISM: Homo sapiens

```
<400> SEQUENCE: 16
gtgaaaggaa agagagaaca aacacccggg agagacatca accaaaatcc agtccccagt      60
tttacagcgt gaaagcactg ggatgcgggt cgtaaacatt ttgtgggctt ggcggagact     120
attacgaccc aaataaatgc actgtgtagc gtgttcacag ggctccgggg cctttcgaaa     180
ggttctctgt ttgcttttg                                                  199

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
gtgaaaggaa agagagaata aatatt                                           26

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
caaaaacaaa caaaaaacct ttc                                              23

<210> SEQ ID NO 19
<211> LENGTH: 199
<212> TYPE: DNA
<213> ORGANISM: Artificial Sequence
<220> FEATURE:
<223> OTHER INFORMATION: Sequence of the locus specific for buccal
      epithelial cells after bisulfite treatment assuming 100%
      unmethylation of all CpG sites

<400> SEQUENCE: 19
gtgaaaggaa agagagaata aatatttggg agagatatta attaaaattt agttttagt       60 tttatagtgt gaaagtattg ggatgtgggt tgtaaatatt ttgtgggttt ggtggagatt     120
attatgattt aaataaatgt attgtgtagt gtgtttatag ggttttgggg tttttgaaa     180 ggttttttgt ttgttttg                                                   199

<210> SEQ ID NO 20
<211> LENGTH: 199
<212> TYPE: DNA
<213> ORGANISM: Homo sapiens

<400> SEQUENCE: 20
gtgaaaggaa agagagaaca aacacccggg agagacatca accaaaatcc agtccccagt      60
tttacagcgt gaaagcactg ggatgcgggt cgtaaacatt ttgtgggctt ggcggagact     120
attacgaccc aaataaatgc actgtgtagc gtgttcacag ggctccgggg cctttcgaaa     180
ggttctctgt ttgcttttg                                                  199
```

MATERIALS AND METHODS FOR DETECTING SOURCE BODY FLUIDS

CROSS-REFERENCE TO A RELATED APPLICATION

This application is a divisional application of U.S. application Ser. No. 15/921,079, filed Mar. 14, 2018, the disclosure of which is incorporated herein by reference in its entirety, including any figures, tables, and drawings.

GOVERNMENT SUPPORT

This invention was made with government support under 2015-R2-CX-0012 awarded by National Institute of Justice. The government has certain rights in the invention.

The Sequence Listing for this application is labeled "SeqList-08Mar18-ST25.txt", which was created on Mar. 8, 2018, and is 6 KB. The Sequence Listing is incorporated herein by reference in its entirety.

BACKGROUND OF THE INVENTION

DNA is used to match a sample retrieved from a crime scene with DNA retrieved from a suspect to identify a connection of the suspect to the crime scene. Current DNA analyses do not permit identifying the source of DNA from a suspect. However, certain forensic cases, such as sexual abuse require confirmation that a DNA from a suspect is from an intimate body fluid.

Techniques currently used for body fluid identification are not based on DNA analysis. For example, microscopic observation of sperms is used to identify semen as a source body fluid or histological staining of glycogen-rich cells is used to identify vaginal cells. However, these tests are not reliable. For example, if the male donor does not produce sperm, the source cannot be identified as semen. Similarly, false negatives can occur because the glycogen content of vaginal cells varies depending on the menstrual cycle and reproductive age; whereas, false positives can occur because buccal and urogenital skin cells (even from males) can have high glycogen.

Certain other methods are based on protein/enzyme reactivity or cell staining and are merely presumptive. These methods may have low sensitivity and render the portion of the sample useless for subsequent analysis. Therefore, forensic laboratories may be left to choose between isolating DNA to compare a suspect's DNA or determining body fluid of origin.

Certain other methods of identifying source body fluid are based on analyzing RNA transcripts. However, the need to identify a body fluid often arises after DNA is isolated. To perform an RNA transcript analysis, the laboratory technician would have to retrieve a new portion of the original sample (if available) and isolate RNA. However, the original sample may have already been consumed.

BRIEF SUMMARY OF THE INVENTION

The invention provides methods that avoid the problems and difficulties with current methods of detecting body fluids in a sample, particularly, a forensic sample. The methods of the invention depend on the analyses of levels of DNA methylation at specific genetic loci to detect specific body fluids.

In one embodiment, the body fluid and/or cells present in the sample comprise vaginal secretion or vaginal epithelial cell, semen or sperm, saliva or buccal epithelial cell, and blood or blood cell.

The level of methylation at specific loci in the genomic DNA isolated from a sample can be determined by high-resolution melt analysis (HRM) of amplicons produced using specific primers designed to amplify the specific loci.

A further embodiment of the invention provides a method for determining the level of methylation at specific loci in the genomic DNA isolated from a cell, for example, a cell suspected to be a vaginal epithelial cell, buccal epithelial cell, sperm, or blood cell isolated from a forensic sample.

Kits containing primers and reagents for carrying out the methods disclosed herein are also provided.

Assays for determining the level of methylation at specific loci in the genomic DNA isolated from a sample are also provided. In certain embodiments, the assays comprise HRM or pyrosequencing of amplicons produced using specific primers designed to amplify specific loci in the genomic DNA.

BRIEF DESCRIPTION OF THE FIGURES

The patent or application file contains at least one drawing executed in color. Copies of this patent or patent application publication with color drawing(s) will be provided by the Office upon request and payment of the necessary fee.

BRIEF DESCRIPTION OF SEQUENCES

Figure 1:
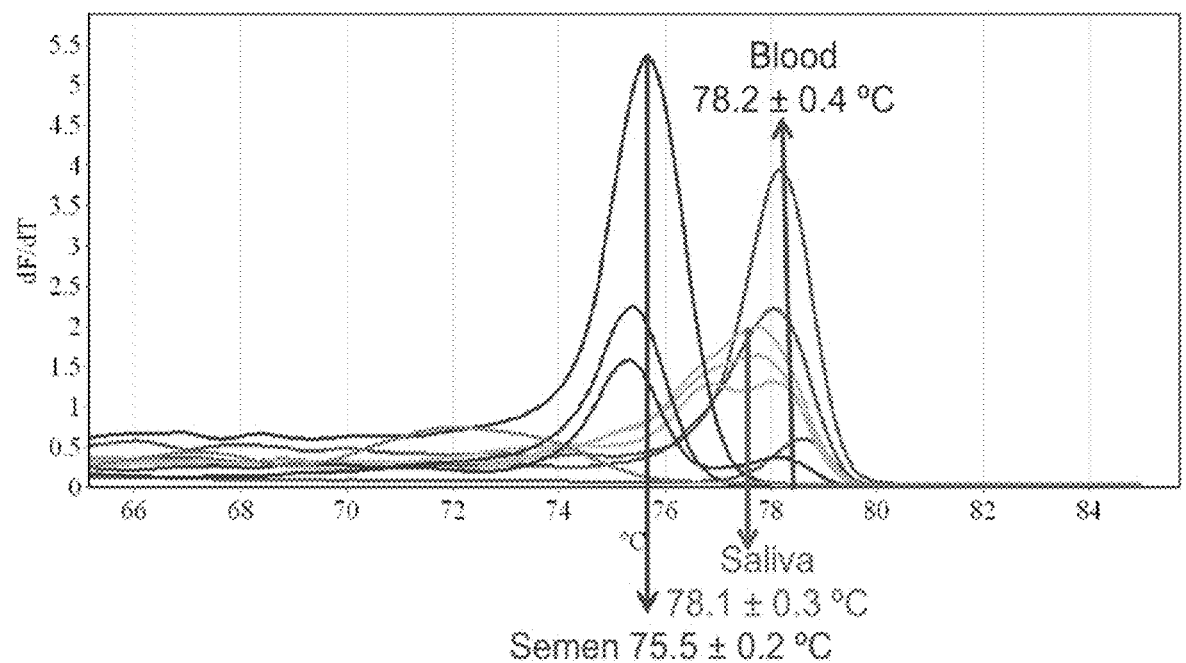
FIG. 1 provides melt curves for the amplified region ZC3H12D, which is located on human chromosome 6. The blue lines represent semen samples and have a lower TM when compared to blood (red lines) and saliva (green lines). For this marker (ZC3H12D), the typical TM for semen is 75.5° C.±0.2° C., whereas the TM for blood is 78.2° C.±0.4° C. and saliva 78.1° C. with 0.3° C. SD.

SEQ ID NO: 1: Sequence of the locus specific for vaginal epithelial cell.

SEQ ID NO: 2: Sequence of a forward primer designed to amplify the locus specific for vaginal epithelial cell.

SEQ ID NO: 3: Sequence of a reverse primer designed to amplify the locus specific for vaginal epithelial cell.

SEQ ID NO: 4: Sequence of the locus specific for vaginal epithelial cell after bisulfite treatment assuming 100% unmethylation of all CpG sites.

SEQ ID NO: 5: Sequence of the locus specific for vaginal epithelial cell after bisulfite treatment assuming 100% methylation of all CpG sites.

SEQ ID NO: 6: Sequence of the locus specific for sperm.

SEQ ID NO: 7: Sequence of a forward primer designed to amplify the locus specific for sperm.

SEQ ID NO: 8: Sequence of a reverse primer designed to amplify the locus specific for sperm.

SEQ ID NO: 9: Sequence of the locus specific for sperm after bisulfite treatment assuming 100% unmethylation of all CpG sites.

SEQ ID NO: 10: Sequence of the locus specific for sperm after bisulfite treatment assuming 100% methylation of all CpG sites.

SEQ ID NO: 11: Sequence of the locus specific for blood cells.

SEQ ID NO: 12: Sequence of a forward primer designed to amplify the locus specific for blood cells.

SEQ ID NO: 13: Sequence of a reverse primer designed to amplify the locus specific for blood cells.

SEQ ID NO: 14: Sequence of the locus specific for blood cells after bisulfite treatment assuming 100% unmethylation of all CpG sites.

SEQ ID NO: 15: Sequence of the locus specific for blood cells after bisulfite treatment assuming 100% methylation of all CpG sites.

SEQ ID NO: 16: Sequence of the locus specific for saliva or buccal epithelial cells.

SEQ ID NO: 17: Sequence of a forward primer designed to amplify the locus specific for buccal epithelial cells.

SEQ ID NO: 18: Sequence of a reverse primer designed to amplify the locus specific for buccal epithelial cells.

SEQ ID NO: 19: Sequence of the locus specific for buccal epithelial cells after bisulfite treatment assuming 100% unmethylation of all CpG sites.

SEQ ID NO: 20: Sequence of the locus specific for buccal epithelial cells after bisulfite treatment assuming 100% methylation of all CpG sites.

DETAILED DESCRIPTION OF THE INVENTION

The subject invention provides materials and methods for detecting body fluids in a sample comprising cells and/or body fluids, for example, a forensic sample, based on DNA analyses. DNA is commonly retrieved from crime scenes, and therefore, DNA isolation, storage, and general use is validated in criminal investigations. The methods described herein are time and cost-effective and require little personnel training. In one embodiment, the invention provides an assay to identify a source body fluid as semen, blood, saliva, or vaginal secretion in a sample.

DNA methylation is one of the epigenetic mechanisms for gene regulation. Different levels of DNA methylation in certain genetic loci control gene expression by silencing or activating specific genes. The presence of a methyl group on the 5' carbon of a cytosine belonging to the dinucleotide CG (CpG) is believed to prevent the binding of the transcription machinery to the promoter of a gene. Some loci on the genome called "tissue-specific differentially methylated regions" can therefore be used for cell identification because they present different levels of DNA methylation depending on the cell studied.

In accordance with the subject invention, DNA methylation levels at specific loci are different for certain cells from body fluids when compared to other cells. For example, DNA methylation levels at specific loci are different for cells from blood, vaginal secretions, saliva, or semen. Accordingly, in certain embodiments of the invention, methylation status at specific genetic loci in the genomic DNA is determined and used to identify the source of body fluid in a sample.

The nucleotide coordinates for genetic loci mentioned herein correspond to University of California Santa Cruz genome browser and Assembly hg19.

Identifying vaginal epithelial cells based on DNA methylation methods provided herein is performed by determining DNA methylation at a vaginal epithelial cell specific locus. In one embodiment, determining DNA methylation at the vaginal epithelial cell specific locus is performed through the use of a specific primer pair that amplifies the vaginal epithelial cell specific locus, having the sequence of SEQ ID NO: 1, from bisulfite-treated genomic DNA. For example, an amplicon corresponding to the vaginal epithelial cell specific locus can be obtained by PCR using bisulfite-treated genomic DNA as template and a primer pair having the sequences of SEQ ID NOs: 2 and 3.

The vaginal epithelial cell specific locus having the sequence of SEQ ID NO: 1 is also referred to as VE_8 in this disclosure. VE_8 is a locus of 131 base pairs on chromosome 16 and occupies the chromosomal location from 86398381 to 86398511. As such, the genome coordinates for VE_8 are chr16: 86398381-86398511. VE_8 locus contains CpG sites that are hypomethylated in the genomes of vaginal epithelial cells compared to other cells, particularly, blood cells, semen, or buccal epithelial cells. Particularly, cytosine residues located at positions 39, 75, 87, and 97 are hypomethylated in the genomes of vaginal epithelial cells compared to other cells, particularly, blood cells, semen, or buccal epithelial cells.

Identifying sperms based on DNA methylation methods provided herein is performed by determining DNA methylation at a sperm specific locus. In one embodiment, determining DNA methylation at the sperm specific locus is performed through the use of a specific primer pair that amplifies a sperm specific locus, having the sequence of SEQ ID NO: 6, from the bisulfite-treated genomic DNA. An amplicon corresponding to the sperm specific locus is obtained by PCR using bisulfite-treated genomic DNA as template and a primer pair having the sequences of SEQ ID NOs: 7 and 8.

The sperm specific locus having the sequence of SEQ ID NO: 6 is also referred to as ZC3H12D in this disclosure. ZC3H12D is a locus of 91 base pairs on chromosome 6 and occupies the chromosomal location from 149778061 to 149778151. The genome coordinates for ZC3H12D are chr6:149778061-149778151. ZC3H12D locus contains CpG sites that are hypomethylated in the genomes of sperms compared to other cells, particularly, blood cells, vaginal epithelial cells, or buccal epithelial cells. Particularly, cytosine residues located at positions 21, 43, 45, 55, 62, and 67 are hypomethylated in the genomes of vaginal epithelial cells compared to other cells, particularly, blood cells, semen, or buccal epithelial cells.

Identifying blood cells based on DNA methylation methods provided herein is performed by determining DNA methylation at a blood cell specific locus. In one embodiment, determining DNA methylation at the blood cell specific locus is performed through the use of a specific primer pair that amplifies a blood cell specific locus, having the sequence of SEQ ID NO: 11, from the bisulfite-treated genomic DNA. An amplicon corresponding to the blood cell specific locus is obtained by PCR using bisulfite-treated genomic DNA as template and a primer pair having the sequences of SEQ ID NOs: 12 and 13.

The blood cell specific locus having the sequence of SEQ ID NO: 11 is also referred to as INPP5D200_TM60 in this disclosure. INPP5D200_TM60 is a locus of 156 base pairs on chromosome 2 and occupies the chromosomal location from 233060162 to 233060317. The genome coordinates for INPP5D200_TM60 are chr2: 233060162-233060317. INPD200_TM60 locus contains CpG sites that are hypomethylated in the genomes of blood cells, particularly, white blood cells, compared to other cells, particularly, vaginal epithelial cells, semen, or buccal epithelial cells. Particularly, cytosine residues located at positions 24, 26, 33, 59, and 130 are hypomethylated in the genomes of vaginal epithelial cells compared to other cells, particularly, blood cells, semen, or buccal epithelial cells.

Identifying buccal epithelial cells based on DNA methylation methods provided herein is performed by determining DNA methylation at a buccal epithelial cell specific locus. In one embodiment, determining DNA methylation at the buccal epithelial cell specific locus is performed through the use of a specific primer pair that amplifies a buccal epithelial cell specific locus, having the sequence of SEQ ID NO: 16, from the bisulfite-treated genomic DNA. An amplicon corresponding to the buccal epithelial cell specific locus is obtained by PCR using bisulfite-treated genomic DNA as template and a primer pair having the sequences of SEQ ID NOs: 17 and 18.

The buccal epithelial cell specific locus having the sequence of SEQ ID NO: 16 is also referred to as VE_15 in this disclosure. VE_15 is a locus of 199 base pairs on chromosome 7 and occupies the chromosomal location from 27199577 to 27199775. The genome coordinates for VE_15 are chr6:27199577-27199775. VE_15 locus contains CpG sites that are hypomethylated in the genomes of sperms compared to other cells, particularly, blood cells, vaginal epithelial cells, or buccal epithelial cells. Particularly, cytosine residues located at positions 27, 68, 86, 91, 125, 150, 166 and 176 are hypomethylated in the genomes of vaginal epithelial cells compared to other cells, particularly, blood cells, semen, or buccal epithelial cells.

The methods described herein can be practiced with minute amounts of genomic DNA, for example, between 1 ng to 50 ng, particularly, between 5 ng to 30 ng, more particularly, at about 20 ng. Moreover, methylation levels at specific loci described herein, for example, SEQ ID NOs: 1, 6, 11, and 16, can be performed when mixtures of body fluids are present.

Accordingly, one embodiment of the invention provides a method for identifying a sample as containing, or not containing, one or more cells selected from a vaginal epithelial cell, a sperm, a blood cell, or a buccal epithelial cell, the method comprising the steps of:
  a) determining the level of methylation at the genetic loci corresponding to one or more of SEQ ID NOs: 1, 6, 11, and 16, in:
    i) a genomic DNA isolated from the sample, and
    ii) optionally, a control genomic DNA;
  b) optionally, obtaining one or more reference values corresponding to the levels of methylation at the genetic loci corresponding to one or more of SEQ ID NOs: 1, 6, 11, and 16; and
  c) identifying the sample as:
    i) containing or not containing the vaginal epithelial cell based on the level of methylation at the genetic locus corresponding to SEQ ID NO: 1 in the genomic DNA isolated from the sample,
    ii) containing or not containing the sperm based on the level of methylation at the genetic locus corresponding to SEQ ID NO: 6 in the genomic DNA isolated from the sample,
    iii) containing or not containing the blood cell based on the level of methylation at the genetic locus corresponding to SEQ ID NO: 11 in the genomic DNA isolated from the sample, and/or
    iv) containing or not containing the buccal epithelial cell based on the level of methylation at the genetic locus corresponding to SEQ ID NO: 16 in the genomic DNA isolated from the sample.

In certain embodiments, the methods described herein to identify a sample as containing a vaginal epithelial cell, sperm, blood cell, or a buccal epithelial cell are practiced on a forensic sample to detect the presence of one or more of these cells in the forensic sample. In certain embodiments, the methods are practiced on a forensic sample that is processed to separate a cell suspected to be a vaginal epithelial cell, sperm, blood cell, or buccal epithelial cell before the step of isolating the genomic DNA. In an even further embodiment, the methods are practiced on a forensic sample that is known to contain only vaginal epithelial cells, sperms, blood cells, or buccal epithelial cells or a combination thereof.

In one embodiment, the invention provides a method for identifying a sample as containing, or not containing, a vaginal epithelial cell, the method comprising the steps of:
  a) determining the level of methylation at the genetic locus corresponding to SEQ ID NO: 1 in:
    i) a genomic DNA isolated from the sample, and
    ii) optionally, a control genomic DNA;
  b) optionally, obtaining one or more reference values corresponding to the level of methylation at the genetic locus corresponding to SEQ ID NO: 1; and
  c) identifying the sample as:
    i) containing or not containing the vaginal epithelial cell based on the level of methylation at the genetic locus corresponding to SEQ ID NO: 1 in the genomic DNA isolated from the sample.

In certain such embodiments, the methods further comprise identifying a sample as containing, or not containing, one or more cells selected from a sperm, a blood cell, and a buccal epithelial cell, the method comprising the steps of:
  a) determining the level of methylation at the genetic loci corresponding to one or more of SEQ ID NOs: 6, 11, and 16, in:
    i) a genomic DNA isolated from the sample, and
    ii) optionally, a control genomic DNA;
  b) optionally, obtaining one or more reference values corresponding to the levels of methylation at the genetic loci corresponding to one or more of SEQ ID NOs: 6, 11, and 16; and
  c) identifying the sample as:
    i) containing or not containing the sperm based on the level of methylation at the genetic locus corresponding to SEQ ID NO: 6 in the genomic DNA isolated from the sample,
    ii) containing or not containing the blood cell based on the level of methylation at the genetic locus corresponding to SEQ ID NO: 11 in the genomic DNA isolated from the sample, and/or
    iii) containing or not containing the buccal epithelial cell based on the level of methylation at the genetic locus corresponding to SEQ ID NO: 16 in the genomic DNA isolated from the sample.

In another embodiment, the invention provides a method for identifying a sample as containing, or not containing, a sperm, the method comprising the steps of:
  a) determining the level of methylation at the genetic locus corresponding to SEQ ID NO: 6 in:
    i) a genomic DNA isolated from the sample, and
    ii) optionally, a control genomic DNA;

b) optionally, obtaining one or more reference values corresponding to the level of methylation at the genetic locus corresponding to SEQ ID NO: 6; and c) identifying the sample as:
   i) containing or not containing the vaginal epithelial cell based on the level of methylation at the genetic locus corresponding to SEQ ID NO: 6 in the genomic DNA isolated from the sample.

In certain such embodiments, the methods further comprise identifying a sample as containing, or not containing, one or more cells selected from a vaginal epithelial cell, a blood cell, and a buccal epithelial cell, the method comprising the steps of:

a) determining the level of methylation at the genetic loci corresponding to one or more of SEQ ID NOs: 1, 11, and 16, in:
   i) a genomic DNA isolated from the sample, and
   ii) optionally, a control genomic DNA;

b) optionally, obtaining one or more reference values corresponding to the levels of methylation at the genetic loci corresponding to one or more of SEQ ID NOs: 1, 11, and 16; and c) identifying the sample as:
   i) containing or not containing the vaginal epithelial cell based on the level of methylation at the genetic locus corresponding to SEQ ID NO: 1 in the genomic DNA isolated from the sample,
   ii) containing or not containing the blood cell based on the level of methylation at the genetic locus corresponding to SEQ ID NO: 11 in the genomic DNA isolated from the sample, and/or
   iii) containing or not containing the buccal epithelial cell based on the level of methylation at the genetic locus corresponding to SEQ ID NO: 16 in the genomic DNA isolated from the sample.

In a further embodiment, the invention provides a method for identifying a sample as containing, or not containing, a blood cell, the method comprising the steps of:

a) determining the level of methylation at the genetic locus corresponding to SEQ ID NO: 11 in:
   i) a genomic DNA isolated from the sample, and
   ii) optionally, a control genomic DNA;

b) optionally, obtaining one or more reference values corresponding to the level of methylation at the genetic locus corresponding to SEQ ID NO: 11; and c) identifying the sample as:
   i) containing or not containing the vaginal epithelial cell based on the level of methylation at the genetic locus corresponding to SEQ ID NO: 11 in the genomic DNA isolated from the sample.

In certain such embodiments, the methods further comprise identifying a sample as containing, or not containing, one or more cells selected from a vaginal epithelial cell, a sperm, and a buccal epithelial cell, the method comprising the steps of:

a) determining the level of methylation at the genetic loci corresponding to one or more of SEQ ID NOs: 1, 6, and 16, in:
   i) a genomic DNA isolated from the sample, and
   ii) optionally, a control genomic DNA;

b) optionally, obtaining one or more reference values corresponding to the levels of methylation at the genetic loci corresponding to one or more of SEQ ID NOs: 1, 6, and 16; and c) identifying the sample as:
   i) containing or not containing the vaginal epithelial cell based on the level of methylation at the genetic locus corresponding to SEQ ID NO: 1 in the genomic DNA isolated from the sample,
   ii) containing or not containing the sperm based on the level of methylation at the genetic locus corresponding to SEQ ID NO: 6 in the genomic DNA isolated from the sample, and/or
   iii) containing or not containing the buccal epithelial cell based on the level of methylation at the genetic locus corresponding to SEQ ID NO: 16 in the genomic DNA isolated from the sample.

In an even further embodiment, the invention provides a method for identifying a sample as containing, or not containing, a buccal epithelial cell, the method comprising the steps of:

a) determining the level of methylation at the genetic locus corresponding to SEQ ID NO: 16 in:
   i) a genomic DNA isolated from the sample, and
   ii) optionally, a control genomic DNA;

b) optionally, obtaining one or more reference values corresponding to the level of methylation at the genetic locus corresponding to SEQ ID NO: 16; and c) identifying the sample as:
   i) containing or not containing the buccal epithelial cell based on the level of methylation at the genetic locus corresponding to SEQ ID NO: 16 in the genomic DNA isolated from the sample.

In certain such embodiments, the methods further comprise identifying a sample as containing, or not containing, one or more cells selected from a vaginal epithelial cell, a sperm, and a blood cell, the method comprising the steps of:

a) determining the level of methylation at the genetic loci corresponding to one or more of SEQ ID NOs: 1, 6, and 11, in:
   i) a genomic DNA isolated from the sample, and
   ii) optionally, a control genomic DNA;

b) optionally, obtaining one or more reference values corresponding to the levels of methylation at the genetic loci corresponding to one or more of SEQ ID NOs: 1, 6, and 11; and c) identifying the sample as:
   i) containing or not containing the vaginal epithelial cell based on the level of methylation at the genetic locus corresponding to SEQ ID NO: 1 in the genomic DNA isolated from the sample,
   ii) containing or not containing the sperm based on the level of methylation at the genetic locus corresponding to SEQ ID NO: 6 in the genomic DNA isolated from the sample, and/or
   iii) containing or not containing the blood cell based on the level of methylation at the genetic locus corresponding to SEQ ID NO: 11 in the genomic DNA isolated from the sample.

In certain embodiments, the methods described herein to identify a sample as containing a vaginal epithelial cell, sperm, blood cell, a buccal epithelial cell, or a combination thereof are practiced on a forensic sample to detect the presence of one or more of these cells in the forensic sample. In certain embodiments, the methods are practiced on a forensic sample that is processed to separate a cell suspected to be a vaginal epithelial cell, sperm, blood cell, buccal epithelial cell, or a combination thereof before the step of isolating the genomic DNA. In an even further embodiment, the methods are practiced on a forensic sample that is known to contain only vaginal epithelial cells, sperms, blood cells, buccal epithelial cells, or a combination thereof. The control sample used in the methods of the invention can be obtained from one or more of the following: a known vaginal epithelial cell, a known sperm, a known blood cell, and a known buccal epithelial cell. The control sample can also be a cell other than a vaginal epithelial cell, sperm, blood cell, or buccal epithelial cell and that is known to have methylation levels at the specific genetic loci corresponding to SEQ ID NOs: 1, 6, 11, and 16 to be different from the methylation levels at SEQ ID NOs: 1, 6, 11, and 16 from a vaginal epithelial cell, sperm, blood cell, and buccal epithelial cell, respectively.

If the control sample is a vaginal epithelial cell, the step of identifying the sample as containing the vaginal epithelial cell is based on the level of methylation at the genetic locus corresponding to SEQ ID NO: 1 in the genomic DNA isolated from the sample being similar to the level of methylation at the genetic locus corresponding to SEQ ID NO: 1 in the control genomic DNA. Also, if the control sample is a vaginal epithelial cell, the step of identifying the sample as not containing the vaginal epithelial cell is based on the level of methylation at the genetic locus corresponding to SEQ ID NO: 1 in the genomic DNA isolated from the sample being different from the level of methylation at the genetic locus corresponding to SEQ ID NO: 1 in the control genomic DNA.

If the control sample is a cell different from a vaginal epithelial cell, the step of identifying the sample as containing the vaginal epithelial cell is based on the level of methylation at the genetic locus corresponding to SEQ ID NO: 1 in the genomic DNA isolated from the sample being different from the level of methylation at the genetic locus corresponding to SEQ ID NO: 1 in the control genomic DNA. Also, if the control sample is a cell different from a vaginal epithelial cell, the step of identifying the sample as not containing the vaginal epithelial cell is based on the level of methylation at the genetic locus corresponding to SEQ ID NO: 1 in the genomic DNA isolated from the sample being similar to the level of methylation at the genetic locus corresponding to SEQ ID NO: 1 in the control genomic DNA.

The reference value corresponding to the level of methylation at the genetic locus corresponding to SEQ ID NO: 1 can indicate the level of methylation at the genetic locus corresponding to SEQ ID NO: 1 in a vaginal epithelial cell or a cell other than a vaginal epithelial cell. As such, the reference value corresponding to level of methylation at the genetic locus corresponding to SEQ ID NO: 1 can indicate the presence or absence of a vaginal epithelial cell. In a vaginal epithelial cell, the genetic locus VE_8 is methylated at less than about 20%, less than about 15%, less than about 10%, less than about 5%, or less than about 1%.

Similarly, if the control sample is a sperm, the step of identifying the sample as containing the sperm is based on the level of methylation at the genetic locus corresponding to SEQ ID NO: 6 in the genomic DNA isolated from the sample being similar to the level of methylation at the genetic locus corresponding to SEQ ID NO: 6 in the control genomic DNA. Also, if the control sample is a sperm, the step of identifying the sample as not containing the sperm is based on the level of methylation at the genetic locus corresponding to SEQ ID NO: 6 in the genomic DNA isolated from the sample being different from the level of methylation at the genetic locus corresponding to SEQ ID NO: 6 in the control genomic DNA.

If the control sample is a cell different from a sperm, the step of identifying the sample as containing the sperm is based on the level of methylation at the genetic locus corresponding to SEQ ID NO: 6 in the genomic DNA isolated from the sample being different from the level of methylation at the genetic locus corresponding to SEQ ID NO: 6 in the control genomic DNA. Also, if the control sample is a cell different from a sperm, the step of identifying the sample as not containing the sperm is based on the level of methylation at the genetic locus corresponding to SEQ ID NO: 6 in the genomic DNA isolated from the sample being similar to the level of methylation at the genetic locus corresponding to SEQ ID NO: 6 in the control genomic DNA.

The reference value corresponding to the level of methylation at the genetic locus corresponding to SEQ ID NO: 6 can indicate the level of methylation at the genetic locus corresponding to SEQ ID NO: 6 in a sperm or a cell other than a sperm. As such, the reference value corresponding to level of methylation at the genetic locus corresponding to SEQ ID NO: 6 can indicate the presence or absence of a sperm. In a sperm, the genetic locus ZC3H12D is methylated at less than about 20%, less than about 15%, less than about 10%, less than about 5%, or less than about 1%

Further, if the control sample is a blood cell, the step of identifying the sample as containing the blood cell is based on the level of methylation at the genetic locus corresponding to SEQ ID NO: 11 in the genomic DNA isolated from the sample being similar to the level of methylation at the genetic locus corresponding to SEQ ID NO: 11 in the control genomic DNA. Also, if the control sample is a blood cell, the step of identifying the sample as not containing the blood cell is based on the level of methylation at the genetic locus corresponding to SEQ ID NO: 11 in the genomic DNA isolated from the sample being different from the level of methylation at the genetic locus corresponding to SEQ ID NO: 11 in the control genomic DNA.

If the control sample is a cell different from a blood cell, the step of identifying the sample as containing the blood cell is based on the level of methylation at the genetic locus corresponding to SEQ ID NO: 11 in the genomic DNA isolated from the sample being different from the level of methylation at the genetic locus corresponding to SEQ ID NO: 11 in the control genomic DNA. Also, if the control sample is a cell different from a blood cell, the step of identifying the sample as not containing the blood cell is based on the level of methylation at the genetic locus corresponding to SEQ ID NO: 11 in the genomic DNA isolated from the sample being similar to the level of methylation at the genetic locus corresponding to SEQ ID NO: 11 in the control genomic DNA.

The reference value corresponding to the level of methylation at the genetic locus corresponding to SEQ ID NO: 11 can indicate the level of methylation at the genetic locus corresponding to SEQ ID NO: 11 in a blood cell or a cell other than a blood cell. As such, the reference value corresponding to level of methylation at the genetic locus corresponding to SEQ ID NO: 11 can indicate the presence or absence of a blood cell. In a blood cell, the genetic locus INPD200_TM60 is methylated at less than about 20%, less than about 15%, less than about 10%, less than about 5%, or less than about 1%.

Furthermore, if the control sample is a buccal epithelial cell, the step of identifying the sample as containing the buccal epithelial cell is based on the level of methylation at the genetic locus corresponding to SEQ ID NO: 16 in the genomic DNA isolated from the sample being similar to the level of methylation at the genetic locus corresponding to SEQ ID NO: 16 in the control genomic DNA. Also, if the control sample is a buccal epithelial cell, the step of identifying the sample as not containing the buccal epithelial cell is based on the level of methylation at the genetic locus corresponding to SEQ ID NO: 16 in the genomic DNA isolated from the sample being different from the level of methylation at the genetic locus corresponding to SEQ ID NO: 16 in the control genomic DNA.

If the control sample is a cell different from a buccal epithelial cell, the step of identifying the sample as containing the buccal epithelial cell is based on the level of methylation at the genetic locus corresponding to SEQ ID NO: 16 in the genomic DNA isolated from the sample being different from the level of methylation at the genetic locus corresponding to SEQ ID NO: 16 in the control genomic DNA. Also, if the control sample is a cell different from a buccal epithelial cell, the step of identifying the sample as not containing the buccal epithelial cell is based on the level of methylation at the genetic locus corresponding to SEQ ID NO: 16 in the genomic DNA isolated from the sample being similar to the level of methylation at the genetic locus corresponding to SEQ ID NO: 16 in the control genomic DNA.

The reference value corresponding to the level of methylation at the genetic locus corresponding to SEQ ID NO: 16 can indicate the level of methylation at the genetic locus corresponding to SEQ ID NO: 16 in a buccal epithelial cell or a cell other than a buccal epithelial cell. As such, the reference value corresponding to level of methylation at the genetic locus corresponding to SEQ ID NO: 16 can indicate the presence or absence of a buccal epithelial cell. In a buccal epithelial cell, the genetic locus VE_15 is methylated at less than about 20%, less than about 15%, less than about 10%, less than about 5%, or less than about 1%.

In one embodiment, the level of methylation of specific genetic loci are used to determine the purity of a preparation of a cell comprising or consisting of one or more of a vaginal epithelial cell, sperm, blood cell, and buccal epithelial cell.

For example, if a vaginal epithelial cell sample is obtained, the level of methylation at the VE_8 locus can be checked in the sample to identify the purity of the vaginal epithelial cells in the sample. For example, if the VE_8 genetic locus is about 100% un-methylated, the vaginal epithelial cell sample is almost 100% pure; whereas, if the VE_8 genetic locus is only about 50% un-methylated, the vaginal epithelial cell sample is not pure and may contain 50% of other types cells, particularly, sperms, blood cells, or buccal epithelial cells.

Similarly, if a sperm sample is obtained, the level of methylation at the ZC3H12D locus can be checked in the sample to identify the purity of the sperm sample. For example, if the ZC3H12D genetic locus is about 100% un-methylated, the sperm sample is almost 100% pure; whereas, if the ZC3H12D genetic locus is only about 50% un-methylated, the sperm sample is not pure and may contain 50% of other types cells, particularly, vaginal epithelial cells, blood cells, or buccal epithelial cells.

Further, if a blood cell sample is obtained, the level of methylation at the INPP5D200_TM60 locus can be checked in the sample to identify the purity of the blood cell sample. For example, if the INPP5D200_TM60 genetic locus is about 100% un-methylated, the blood cell sample is almost 100% pure; whereas, if the INPP5D200_TM60 genetic locus is only about 50% un-methylated, the blood cell sample is not pure and may contain 50% of other types cells, particularly, vaginal epithelial cells, sperms, or buccal epithelial cells.

Furthermore, if a buccal epithelial cell sample is obtained, the level of methylation at the VE_15 locus can be checked in the sample to identify the purity of the buccal epithelial cell sample. For example, if the VE_15 genetic locus is about 100% un-methylated, the buccal epithelial cell sample is almost 100% pure; whereas, if the VE_15 genetic locus is only about 50% un-methylated, the buccal epithelial cell sample is not pure and may contain 50% of other types cells, particularly, vaginal epithelial cells, sperms, or blood cells.

Various techniques are known to a person of ordinary skill in the art to determine the level of methylation at the specific loci in a genomic DNA. Non-limiting examples of such techniques include bisulfite conversion, HRM, digestion by restriction enzymes followed by PCR, Combined Bisulfite Restriction Analysis (COBRA), direct sequencing, cloning and sequencing, bisulfite treatment and sequences, bisulfite treatment and pyrosequencing, mass spectrometry analysis or probe/microarray based assay. Certain techniques of determining methylation at certain genomic sites are described in Eads et al., Xiong et al., Paul et al., Warnecke et al., Tost et al., and Ehrich et al., the contents of which are herein incorporated in their entirety. Additional techniques for determining the level of methylation at a genetic are known to a person of ordinary skill in the art and such techniques are within the purview of the invention.

In a particular embodiment, the levels of methylation at the specific loci in a genomic DNA obtained from a sample are determined by HRM. HRM involves bisulfite treatment of genomic DNA. Bisulfite treatment of genomic DNA chemically changes the unmethylated cytosines to uracil, while the methylated cytosines are unchanged. In the PCR reaction using primers designed to amplify a specific locus, uracils are copied as thymines making the PCR product produced from an un-methylated locus thymine-rich, thereby reducing the melting temperature (TM) of the amplicon compared to the PCR product produced from a methylated locus, which is cytosine-rich. As such, methylation of the specific locus can be determined based on TM of the amplicon, i.e., higher TM indicates a methylated locus and lower TM indicates an un-methylated locus. This technique is referred HRM.

Determining the levels of methylation at the specific loci in a genomic DNA obtained from a sample by HRM comprises the steps of: obtaining the sample, isolating genomic DNA from the sample, treating the isolated DNA with bisulfite, PCR amplifying the genetic loci using specifically designed primers to produce amplicons corresponding to the genetic loci, determining the melting temperatures of the amplicons produced in the PCR, determining the levels of methylation at the specific loci in a genomic DNA based on the melting temperatures of the amplicons. The methylation status at the specific genetic loci can be used to identify the source of body fluid based.

In one embodiment of the invention, amplification and melt analysis are performed in a single instrument, namely, a real time PCR instrument with melt capacity. Use of a single instrument diminishes the hands-on time making the methods efficient.

In one embodiment, a primer pair designed to amplify the genetic locus corresponding to SEQ ID NO: 1 comprises a forward primer comprising SEQ ID NO: 2 and a reverse primer comprising SEQ ID NO: 3. A skilled artisan can design primer pairs other than SEQ ID NOs: 2 and 3 to amplify the genetic locus VE_8 based on the sequence of SEQ ID NO: 1 and the sequences of the regions flanking VE_8 in the genomic DNA. Such embodiments are within the purview of the invention.

In another embodiment, a primer pair designed to amplify the genetic locus corresponding to SEQ ID NO: 6 comprises a forward primer comprising SEQ ID NO: 7 and a reverse primer comprising SEQ ID NO: 8. A skilled artisan can design primer pairs other than SEQ ID NOs: 7 and 8 to amplify the genetic locus ZC3H12D based on the sequence of SEQ ID NO: 6 and the sequences of the regions flanking ZC3H12D in the genomic DNA. Such embodiments are within the purview of the invention.

In a further embodiment, a primer pair designed to amplify the genetic locus corresponding to SEQ ID NOs: 11 comprises a forward primer comprising SEQ ID NO: 12 and a reverse primer comprising SEQ ID NO: 13. A skilled artisan can design primer pairs other than SEQ ID NOs: 12 and 13 to amplify the genetic locus INPD200_TM60 based on the sequences of SEQ ID NOs: 11 and the sequences of regions flanking INPD200_TM60 in the genomic DNA. Such embodiments are within the purview of the invention.

In an even further embodiment, a primer pair designed to amplify the genetic locus corresponding to SEQ ID NOs: 16 comprises a forward primer comprising SEQ ID NO: 17 and a reverse primer comprising SEQ ID NO: 18. A skilled artisan can design primer pairs other than SEQ ID NOs: 17 and 18 to amplify the genetic locus VE_15 based on the sequence of SEQ ID NOs: 16 and the sequences of the regions flanking VE_15 in the genomic DNA. Such embodiments are within the purview of the invention.

Accordingly, in one embodiment, the invention provides a method for identifying a sample as containing, or not containing, one or more cells selected from a vaginal epithelial cell, a sperm, a blood cell, or a buccal epithelial cell, the method comprising the steps of:
 a) isolating genomic DNA from the sample and optionally, a control sample;
 b) treating the isolated genomic DNA with bisulfite;
 c) PCR amplifying the genetic loci corresponding to one or more of SEQ ID NOs: 1, 6, 11, and 16 to produce the corresponding one or more amplicons, wherein the PCR amplifying is performed using one or more primer pairs selected from:
  i) SEQ ID NOs: 2 and 3,
  ii) SEQ ID NOs: 6 and 7,
  iii) SEQ ID NOs: 12 and 13, or
  iv) SEQ ID NOs: 17 and 18; and
 d) determining the melting temperatures of the one or more amplicons; and
 e) identifying the sample as:
  i) containing or not containing the vaginal epithelial cell based on the melting temperature of the amplicon corresponding to the genetic locus corresponding to SEQ ID NO: 1 in the genomic DNA isolated from the sample,
  ii) containing or not containing the sperm based on the melting temperature of the amplicon corresponding to the genetic locus corresponding to SEQ ID NO: 6 in the genomic DNA isolated from the sample,
  iii) containing or not containing the blood cell based on the melting temperature of the amplicon corresponding to the genetic locus corresponding to SEQ ID NO: 11 in the genomic DNA isolated from the sample, and/or
  iv) containing or not containing the buccal epithelial cell based on the melting temperature of the amplicon corresponding to the genetic locus corresponding to SEQ ID NO: 16 in the genomic DNA isolated from the sample.

In a specific embodiment, the invention provides a method for identifying a sample as containing, or not containing a vaginal epithelial cell based on the methylation level of SEQ ID NO: 1 determined using the primer pair of SEQ ID NO: 2 and 3. Such methods can further comprise identifying a sample as containing, or not containing, one or more cells selected from a sperm, a blood cell, and a buccal epithelial cell, based on the methylation level of one or more of SEQ ID NOs: 6, 11, and 16 determined using the primer pairs of SEQ ID NOs: 6 and 7, 12 and 13, and 17 and 18, respectively.

In another embodiment, the invention provides a method for identifying a sample as containing, or not containing a sperm based on the methylation level of SEQ ID NO: 6 determined using the primer pair of SEQ ID NO: 6 and 7. Such methods can further comprise identifying a sample as containing, or not containing, one or more cells selected from a vaginal epithelial cell, a blood cell, and a buccal epithelial cell, based on the methylation level of one or more of SEQ ID NOs: 1, 11, and 16 determined using the primer pairs of SEQ ID NOs: 2 and 3, 12 and 13, and 17 and 18, respectively.

In a further embodiment, the invention provides a method for identifying a sample as containing, or not containing a blood cell based on the methylation level of SEQ ID NO: 11 determined using the primer pair of SEQ ID NO: 12 and 13. Such methods can further comprise identifying a sample as containing, or not containing, one or more cells selected from a vaginal epithelial cell, a sperm, and a buccal epithelial cell, based on the methylation level of one or more of SEQ ID NOs: 1, 6, and 16 determined using the primer pairs of SEQ ID NOs: 2 and 3, 6 and 7, and 17 and 18, respectively.

In an even further embodiment, the invention provides a method for identifying a sample as containing, or not containing a buccal epithelial cell based on the methylation level of SEQ ID NO: 16 determined using the primer pair of SEQ ID NO: 17 and 18. Such methods can further comprise identifying a sample as containing, or not containing, one or more cells selected from a vaginal epithelial cell, a sperm, and a blood cell based on the methylation level of one or more of SEQ ID NOs: 1, 6, and 11 determined using the primer pairs of SEQ ID NOs: 2 and 3, 6 and 7, and 12 and 13, respectively.

In certain embodiments, the methods described herein to identify a sample as containing a vaginal epithelial cell, sperm, blood cell, or a buccal epithelial cell are practiced on a forensic sample to detect the presence of one or more of these cells in the forensic sample. In certain embodiments, the methods are practiced on a forensic sample that is processed to separate a cell suspected to be a vaginal epithelial cell, sperm, blood cell, or buccal epithelial cell before the step of isolating the genomic DNA.

In one embodiment, the melting temperature of one or more amplicons corresponding to the genetic loci corresponding to SEQ ID NOs: 1, 6, 11, and 16 are compared to a reference value to determine the methylation status of the genetic loci corresponding to SEQ ID NOs: 1, 6, 11, and 16, which in turn is used to identify the sample as containing or not containing one or more cells selected from a vaginal epithelial cell, a sperm, a blood cell, or a buccal epithelial cell.

In one embodiment, the melting temperature of about 76.6° C. for the amplicon corresponding to the genetic loci corresponding to SEQ ID NO: 1 is used to identify the presence of a vaginal epithelial cell in the sample; whereas, the melting temperature of about 78.1° C. for the amplicon corresponding to the genetic loci corresponding to SEQ ID NO: 1 is used to identify the absence of a vaginal epithelial cell in the sample.

In another embodiment, the melting temperature of about 75.5° C. for the amplicon corresponding to the genetic loci corresponding to SEQ ID NO: 6 is used to identify the presence of a sperm in the sample; whereas, the melting temperature of about 78.2° C. for the amplicon corresponding to the genetic loci corresponding to SEQ ID NO: 1 is used to identify the absence of a sperm in the sample.

In a further embodiment, the melting temperature of about 80° C. for the amplicon corresponding to the genetic loci corresponding to SEQ ID NO: 11 is used to identify the presence of a blood cell in the sample; whereas, the melting temperature of about 83° C. for the amplicon corresponding to the genetic loci corresponding to SEQ ID NO: 11 is used to identify the absence of a blood cell in the sample.

Figure 3:
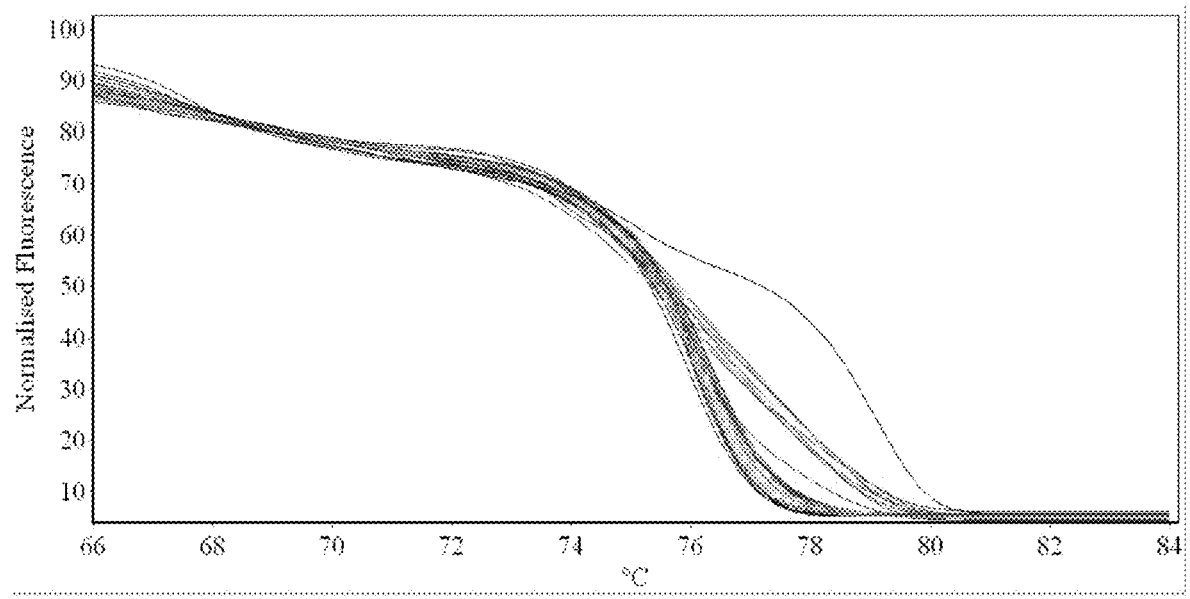
FIG. 3 provides melt curves (normalized fluorescence versus temperature in degree Celsius) for the amplified region VE_15. The pink lines represent DNA samples from vaginal epithelia, blue represents semen, red represents blood and green represents saliva.

In an even further embodiment, the identification of saliva is made depending on the shape of the normalized curve for the graph of fluorescence versus temperature in a melting curve analysis of the amplicon corresponding to the genetic loci corresponding to SEQ ID NO: 16. Typically, unmethylated and methylated controls are run in a melting curve analysis of a sample and a saliva sample displays a curve that is intermediate between the unmethylated control and methylated control. The other body fluids and cells, for example, semen, blood, and vaginal epithelial cells show a curve similar to unmethylated control (FIG. 3).

The four primer sets described above would amplify genomic DNA isolated from samples containing one or more of vaginal epithelial cells or vaginal secretions, sperms or semen, blood or blood cells, and buccal epithelial cell or saliva. The identification of different body fluids is made only after amplification and further analysis, for example, HRM or sequencing analysis.

The primer pairs amplify bisulfite treated genomic DNA regardless of its methylation status and would not amplify genomic DNA that is not bisulfite treated. Therefore, if the DNA sample is not appropriate for PCR amplification, for example, due to a low amount of DNA or presence of impurities, the amplicons will not be produced.

A control DNA sample added can be used and treated in the same manner as a test sample to ensure that the reagents are working properly. Therefore, if a test sample fails to produce amplicons, the sample can be identified as a source of a problem for lack of amplification despite having working reagents. Likewise a negative control can be run where water replaces the genomic DNA to ensure that any amplification is not due to unspecific amplification arising from contaminated reagents.

A control primer pair can also be used that would amplify genomic DNA that is not bisulfite converted. The presence of an amplicon for this primer pair would tell a user that the bisulfite conversion was not successful. Therefore, instead of having an amplification that did not work for an unknown reason, a user would identify a failed bisulfite conversion.

In one embodiment, an amplicon corresponding to a genetic locus is distinguished from other amplicons based on a fluorophore attached to the primer pair designed to amplify the genetic locus. Different fluorophores attached to different primer pairs can be detected at different wavelengths using fluorescence detectors.

In one embodiment, each amplicon is labelled with a fluorophore and different fluorophores are matched with different melt curves. By matching fluorophores with melt curves, the presence of different body fluids in a sample containing a mixture of body fluids can be detected.

In another embodiment, each primer pair is labelled with a fluorophore that is detected at a specific wavelength. As the multiplex PCR proceeds, the fluorophore in the primers is quenched by a nucleotide that specifically binds to the DNA amplicon. Fluorescence decreases with the increase of amplification for that specific locus.

An example of detecting different fluorophores for different primer pairs is provided in the Plexor® qPCR and RT-PCR from Promega, Inc. Certain details of Plexor® qPCR are provided in Technical Manual for Plexor® qPCR (Promega, Literature # TM262, Revised 09/09), the contents of which are herein incorporated by reference in its entirety.

In certain embodiments, a control genomic DNA can comprise DNA that is not bisulfite treated. Therefore, each locus has a "control primer set" directed to a bisulfite untreated genomic DNA sequence and a "test primer sequence" directed to bisulfite treated genomic DNA. Therefore, for every test, one can have a multiplex primer set directed to a bisulfite treated test genomic DNA and a multiplex primer set directed to a bisulfite untreated control genomic DNA.

In a particular embodiment, the levels of methylation at the specific loci in a genomic DNA obtained from a sample are performed by sequencing, for example, pyrosequencing. Determining methylation of a genetic locus based on sequencing involves bisulfite treating a genomic DNA. Bisulfate treatment of genomic DNA chemically changes the unmethylated cytosines to uracil, while the methylated cytosines are unchanged. In the PCR reaction using primers designed to amplify a specific locus, uracils are copied as thymines in an un-methylated locus and cytosines are copied as guanines. As such, methylation of the specific locus can be determined based on the presence of cytosine in the amplicon; whereas, lack of methylation can be determined based on the presence of cytosine in the amplicon.

Determining the levels of methylation at the specific loci in a genomic DNA obtained from a sample by sequencing comprises the steps of: obtaining the sample, isolating genomic DNA from the sample, treating the isolated DNA with bisulfite, PCR amplifying the genetic loci using specifically designed primers to produce amplicons corresponding to the genetic loci, determining the sequences of the amplicons produced in the PCR, and determining the levels of methylation at the specific loci in a genomic DNA based on sequences of the amplicons. The methylation status at the specific genetic loci can be used to identify the source of body fluid based.

Accordingly, in one embodiment, the invention provides a method for identifying a sample as containing or not containing one or more cells selected from a vaginal epithelial cell, a sperm, a blood cell, or a buccal epithelial cell, the method comprising the steps of:
  a) isolating genomic DNA from the sample and optionally, a control sample;
  b) treating the isolated genomic DNA with bisulfite;
  c) PCR amplifying the genetic loci genetic loci corresponding to one or more of SEQ ID NOs: 1, 6, 11, and 16 to produce the corresponding one or more amplicons, wherein the PCR amplifying is performed using one or more primer pairs selected from
    i) SEQ ID NOs: 2 and 3,
    ii) SEQ ID NOs: 6 and 7,
    iii) SEQ ID NOs: 12 and 13, or
    iv) SEQ ID NOs: 17 and 18; and
  d) determining the sequences of the one or more amplicons; and
  e) identifying the sample as:
    i) containing or not containing the vaginal epithelial cell based on the sequence of the amplicon corresponding to the genetic locus corresponding to SEQ ID NO: 1 in the genomic DNA isolated from the sample, ii) containing or not containing the sperm based on the sequence of the amplicon corresponding to the genetic locus corresponding to SEQ ID NO: 6 in the genomic DNA isolated from the sample, iii) containing or not containing the blood cell based on the sequence of the amplicon corresponding to the genetic locus corresponding to SEQ ID NO: 11 in the genomic DNA isolated from the sample, and/or iv) containing or not containing the buccal epithelial cell based on the sequence of the amplicon corresponding to the genetic locus corresponding to SEQ ID NO: 16 in the genomic DNA isolated from the sample.

In certain embodiments, the methods described herein to identify a sample as containing a vaginal epithelial cell, sperm, blood cell, or a buccal epithelial cell are practiced on a forensic sample to detect the presence of one or more of these cells in the forensic sample. In certain embodiments, the methods are practiced on a forensic sample that is processed to separate a cell suspected to be a vaginal epithelial cell, sperm, blood cell, or buccal epithelial cell before the step of isolating the genomic DNA.

In one embodiment, the sequence of one or more amplicons corresponding to the genetic loci corresponding to SEQ ID NOs: 1, 6, 11, or 16 are compared to a reference sequence to determine the methylation status of the genetic loci corresponding to SEQ ID NOs: 1, 6, 11, or 16, which in turn is used to identify the sample as containing or not containing one or more cells selected from a vaginal epithelial cell, a sperm, a blood cell, or a buccal epithelial cell.

A skilled artisan can design a sequencing primer to sequence the amplicons corresponding to the genetic loci corresponding to SEQ ID NOs: 1, 6, 11, or 16 based on the sequences of these genetic loci and the sequences of the regions flanking these genetic loci in the genomic DNA. Such embodiments are within the purview of the invention.

In another embodiment, a sequencing primer can be designed based on an adapter introduced into the amplicon by incorporating the adapter into one of the forward or reverse primers. An "adapter" as used herein is a sequence of about 10 to 20 nucleotides that can be introduced into an amplicon by incorporating the adapter into the primer used for the amplification of the amplicon. Once an amplicon contains an adapter sequence, a primer designed based on the sequence of the adapter can be used to sequence the amplicon.

One embodiment of the invention provides a method for determining the levels of methylation at genetic loci corresponding to one or more of SEQ ID NOs: 1, 6, 11, and 16, in a genomic DNA from a cell, the method comprising the steps of:

(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the one or more of the genetic loci corresponding to one or more of SEQ ID NOs: 1, 6, 11, and 16, and
(d) analyzing the PCR amplicons produced in step c) to determine the level of methylation at the genetic loci corresponding to one or more of SEQ ID NOs: 1, 6, 11, and 16.

In a specific embodiment, the invention provides a method for determining the levels of methylation at the genetic locus corresponding to SEQ ID NO: 1 in a genomic DNA from a cell, the method comprising the steps of:

(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the genetic locus corresponding SEQ ID NO: 1, and
(d) analyzing the PCR amplicons produced in step c) to determine the level of methylation at the genetic locus corresponding to SEQ ID NO: 1.

Certain such embodiments further comprise determining the levels of methylation at genetic loci corresponding to one or more of SEQ ID NOs: 6, 11, and 16, in a genomic DNA from a cell, the method comprising the steps of:

(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the one or more of the genetic loci corresponding to one or more of SEQ ID NOs: 6, 11, and 16, and
(d) analyzing the PCR amplicons produced in step c) to determine the level of methylation at the genetic loci corresponding to one or more of SEQ ID NOs: 6, 11, and 16.

In another embodiment, the invention provides a method for determining the levels of methylation at the genetic locus corresponding to SEQ ID NO: 6 in a genomic DNA from a cell, the method comprising the steps of:

(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the genetic locus corresponding SEQ ID NO: 6, and
(d) analyzing the PCR amplicons produced in step c) to determine the level of methylation at the genetic locus corresponding to SEQ ID NO: 6.

Certain such embodiments further comprise determining the levels of methylation at genetic loci corresponding to one or more of SEQ ID NOs: 1, 11, and 16, in a genomic DNA from a cell, the method comprising the steps of:

(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the one or more of the genetic loci corresponding to one or more of SEQ ID NOs: 1, 11, and 16, and
(d) analyzing the PCR amplicons produced in step c) to determine the level of methylation at the genetic loci corresponding to one or more of SEQ ID NOs: 1, 11, and 16.

In a further embodiment, the invention provides a method for determining the levels of methylation at the genetic locus corresponding to SEQ ID NO: 11 in a genomic DNA from a cell, the method comprising the steps of:

(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the genetic locus corresponding SEQ ID NO: 11, and
(d) analyzing the PCR amplicons produced in step c) to determine the level of methylation at the genetic locus corresponding to SEQ ID NO: 11.

Certain such embodiments further comprise determining the levels of methylation at genetic loci corresponding to one or more of SEQ ID NOs: 1, 6, and 16, in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the one or more of the genetic loci corresponding to one or more of SEQ ID NOs: 1, 6, and 16, and
(d) analyzing the PCR amplicons produced in step c) to determine the level of methylation at the genetic loci corresponding to one or more of SEQ ID NOs: 1, 6, and 16.

In an even further embodiment, the invention provides a method for determining the levels of methylation at the genetic locus corresponding to SEQ ID NO: 16 in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the genetic locus corresponding SEQ ID NO: 16, and
(d) analyzing the PCR amplicons produced in step c) to determine the level of methylation at the genetic locus corresponding to SEQ ID NO: 16.

Certain such embodiments further comprise determining the levels of methylation at genetic loci corresponding to one or more of SEQ ID NOs: 1, 6, and 11, in a genomic DNA from a cell, the method comprising the steps of:
(a) isolating the genomic DNA from the cell,
(b) treating the genomic DNA with bisulfite,
(c) conducting a PCR using the bisulfite treated genomic DNA as a template and one or more primer pairs designed to produce amplicons corresponding to the one or more of the genetic loci corresponding to one or more of SEQ ID NOs: 1, 6, and 11, and
(d) analyzing the PCR amplicons produced in step c) to determine the level of methylation at the genetic loci corresponding to one or more of SEQ ID NOs: 1, 6, and 11.

The details described above regarding the techniques for determining the level of methylation at the genetic loci corresponding to one or more SEQ ID NOs: 1, 6, 11, or 16 in the genomic DNA in a sample based on the analysis of the amplicons produced in the PCR amplification steps are also applicable to the method for determining the levels of methylation at these genetic loci. The primer pairs designed to amplify these genetic loci, sequencing primers and other details described above are also applicable to the method for determining the levels of methylation at these genetic loci.

A further embodiment of the invention provides a kit comprising one or more primer pairs designed to amplify the genetic loci corresponding to one or more SEQ ID NOs: 1, 6, 11, or 16 in a bisulfite treated human genomic DNA. In one embodiment, the kit comprises one or more primer pairs selected from:
i) a primer pair having the sequences of SEQ ID NOs: 2 and 3,
ii) a primer pair having the sequences of SEQ ID NOs: 6 and 7,
iii) a primer pair having the sequences of SEQ ID NOs: 12 and 13, and
iv) a primer pair having the sequences of SEQ ID NOs: 17 and 18.

A skilled artisan can design additional primer pairs to amplify the genetic loci corresponding to one or more SEQ ID NOs: 1, 6, 11, or 16 based on the sequences of these genetic loci and the sequences of flanking regions in the genomic DNA and such embodiments are within the purview of the invention.

In one embodiment, the invention provides a kit comprising a primer pair of SEQ ID NOs: 2 and 3, optionally, further comprising, one or more primer pairs selected from:
i) a primer pair having the sequences of SEQ ID NOs: 6 and 7,
ii) a primer pair having the sequences of SEQ ID NOs: 12 and 13, and
iii) a primer pair having the sequences of SEQ ID NOs: 17 and 18.

In another embodiment, the invention provides a kit comprising a primer pair of SEQ ID NOs: 6 and 7, optionally, further comprising, one or more primer pairs selected from:
i) a primer pair having the sequences of SEQ ID NOs: 2 and 3,
ii) a primer pair having the sequences of SEQ ID NOs: 12 and 13, and
iii) a primer pair having the sequences of SEQ ID NOs: 17 and 18.

In a further embodiment, the invention provides a kit comprising a primer pair of SEQ ID NOs: 12 and 13, optionally, further comprising, one or more primer pairs selected from:
i) a primer pair having the sequences of SEQ ID NOs: 2 and 3,
ii) a primer pair having the sequences of SEQ ID NOs: 6 and 7, and
iii) a primer pair having the sequences of SEQ ID NOs: 17 and 18.

In an even further embodiment, the invention provides a kit comprising a primer pair of SEQ ID NOs: 17 and 18, optionally, further comprising, one or more primer pairs selected from:
i) a primer pair having the sequences of SEQ ID NOs: 2 and 6,
ii) a primer pair having the sequences of SEQ ID NOs: 6 and 7, and
iii) a primer pair having the sequences of SEQ ID NOs: 12 and 13.

In further embodiments, the kit comprises one or more reagents, for example, reagents for treating a sample, reagents for isolating cells from the sample, reagents for isolating genomic DNA from the sample, reagents for bisulfite treating the genomic DNA, reagents for conducting PCR, and reagents for conducting pyrosequencing.

As used herein, the singular forms "a," "an" and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%). In the context of melting temperatures where the term "about" is used, the melting temperatures are within 0.45° C. of the stated melting temperature.

As used herein, the term "level of methylation" or "methylation status" as applied to a genetic locus refers to whether one or more cytosine residues present in a CpG have or do not have a methylation group. The level of methylation or methylation status refers to the percentage of cells in a sample that do or do not have a methylation group on such cytosines. For example, if 50 cells in a pool of 100 cells contain methylated cytosines at a CpG site, the level of methylation or methylation status of the CpG site is 50%.

A primer pair is a pair of oligonucleotides, each having about 15 to 25 nucleotides, and designed to amplify a specific locus from template DNA. Guidelines for designing a primer pair to amplify a specific locus to in a template DNA are well known in the art.

A singleplex PCR is a reaction where only one set of primers is used per reaction; whereas, a multiplex reaction is one that uses multiple primer sets per PCR reaction.

MATERIALS AND METHODS

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Designing Primers for Genomic Loci Specific for a Body Fluid

DNA from known body fluids are used in single reactions, i.e., in a singleplex. Initially primer pairs in singleplex PCR reactions are tested. The primers are designed herein to amplify a specific locus in the genomic DNA regardless of methylation status of the genomic locus. Because amplification is independent of methylation, for body fluid identification the primers are designed to amplify a region that presents a different methylation status for the target body fluid when compared to the other body fluids, allowing distinction by TM analysis (FIG. 1).

Multiplex analysis is performed with two, three, or four primer pairs. The primer pairs can be selected from:

i) a primer pair (VE_8) designed to amplify a specific locus in the genomic DNA from vaginal epithelial cells, ii) a primer pair (INPD200_TM60) designed to amplify a specific locus in the genomic DNA from blood, iii) a primer pair (ZC3H12D) designed to amplify a specific locus in the genomic DNA from vaginal semen, iv) a primer pair (VE_15) designed to amplify a specific locus in the genomic DNA from saliva.

Figure 2:
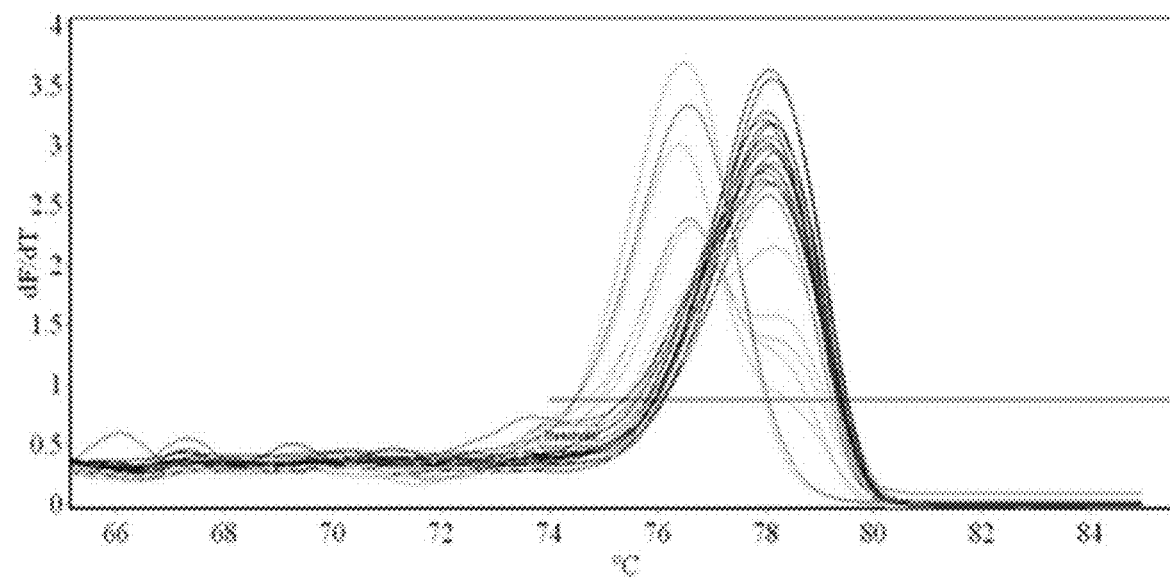
FIG. 2 provides melt curves (−dF/dT) for the amplified region VE_8 (cg08751438). The pink lines represent DNA samples from vaginal epithelia, blue represents semen, red represents blood and green represents saliva.
Figure 4:
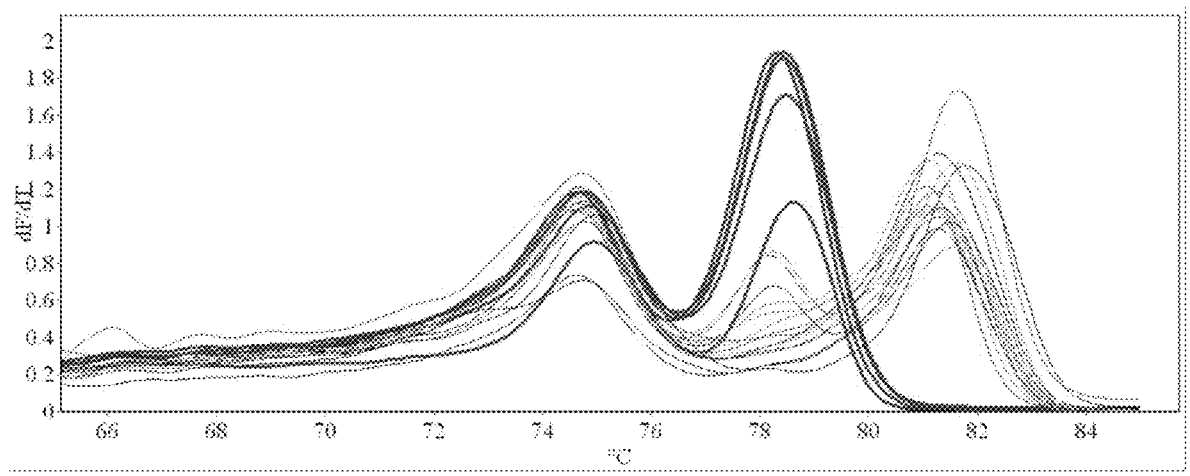
FIG. 4 provides melt curves (normalized fluorescence versus temperature in degree Celsius) for the amplified region INPP5D200_TM60. Orange lines represent DNA samples from vaginal epithelia, blue represents semen, red represents blood and green represents saliva.

Multiplex reactions using two, three, or four primer pairs are used to obtain a melt curve with all the expected TMs (FIGS. 2-4).

Also, Table 1, below shows averages of melting temperature ($T_M$, °C.) and standard deviation (SD) for 10 samples of each body fluid and 4 samples (INPP5D200_TM60) or 5 samples (VE_8) of each control amplified with primers specific for the two loci INPP5D200_TM60 and VE_8. UnM means the unmethylated control and M represents the methylated control.

TABLE 1

Melting averages for cell specific loci disclosed herein.

| Target Body Fluid | Marker Name | 'cg' code | $T_M$(° C.) ± SD | | | | | |
|---|---|---|---|---|---|---|---|---|
| | | | Blood | Saliva | Semen | VE | UnM | M |
| Blood | INPP5D200_TM60 | cg00438740 | 80.0 ± 0.13 | 83.0 ± 0.24 | 83.0 ± 0.30 | 83.0 ± 0.45 | 80.0 ± 0.20 | 83.0 ± 0.17 |
| VE | VE_8 | cg08751438 | 78.1 ± 0.12 | 78.1 ± 0.11 | 78.1 ± 0.10 | 76.6 ± 0.16 | 76.5 ± 0.11 | 78.1 ± 0.06 |

REFERENCES

1. An et al., Body fluid identification in forensics. *Bmb Reports*. 2012, 45(10):545-53.
2. Antunes et al., Tissue-Specific DNA Methylation Patterns in Forensic Samples Detected by Pyrosequencing®. In: Lehmann U, Tost J, editors. Methods in Molecular Biology. Springer New York; 2015. p. 397-409.
3. Antunes et al., Forensic discrimination of vaginal epithelia by DNA methylation analysis through pyrosequencing. *Electrophoresis*. 2016; 37(21):2751-2758.
4. Antunes et al., High-resolution melt analysis of DNA methylation to discriminate semen in biological stains. *Analytical Biochemistry*. 2016, 494, 40-45.
5. Du, P. et al., Comparison of Beta-value and M-value methods for quantifying methylation levels by microarray analysis. *BMCB ioinformatics*. 2010, 11:587
6. Eads et al., Combined bisulfite restriction analysis (COBRA). *Methods Molecular Biology*. 2002; 200:71-85.

7. Ehrich et al. Quantitative high-throughput analysis of DNA methylation patterns by base-specific cleavage and mass spectrometry. *Proceedings of the National Academy of Sciences.* 2005; 102:15785-90.
8. Fraga et al., Epigenetic differences arise during the lifetime of monozygotic twins. *Proceedings of the National Academy of Sciences.* 2005, 102(30):10604-9.
9. Grskovic B et al., DNA methylation: the future of crime scene investigation? Molecular *Biology Reports.* 2013, 40(7):4349-60.
10. Haas et al., mRNA profiling for the identification of blood—results of a collaborative EDNAP exercise. *Forensic Science International: Genetics.* 2011, (1):21-6.
11. Harbison et al., Forensic body fluid identification: state of the art. *Research and Reports in Forensic Medical Science.* 2016, 6:11-23.
12. Juusola et al., mRNA profiling for body fluid identification by multiplex quantitative RT-PCR. *Journal of Forensic Sciences.* 2007, 52(6):1252-62.
13. Li, et al., R. MethPrimer: designing primers for methylation PCRs. *Bioinformatics.* 2002, 18:1427-1431.
14. Park et al., Identification of body fluid-specific DNA methylation markers for use in forensic science. *Forensic Science International-Genetics.* 2014, 13:147-153.
15. Paul et al., Cytosine methylation: quantitation by automated genomic sequencing and GENESCAN analysis. *Biotechniques.* 1996, 21:126-33.
16. Tost et al., Analysis of gene-specific DNA methylation patterns by pyrosequencing technology. *Methods Molecular Biology.* 2007, 373:89-102.
17. Tusnady et al., BiSearch: primer-design and search tool for PCR on bisulfite-treated genomes. *Nucleic Acids Research.* 2005, 33.
18. Warnecke et al., Identification and resolution of artifacts in bisulfite sequencing. *Methods.* 2002, 27:101-7.
19. Xiong Z et al., COBRA: a sensitive and quantitative DNA methylation assay. *Nucleic Acids Research.* 1997, 25:2532-4.

We claim:

1. A method for identifying a sample as containing or not containing a blood cell, the method comprising the steps of:
   (a) determining the level of methylation at the genetic locus of SEQ ID NO: 11 in:
      i) a genomic DNA isolated from the sample, and
      ii) optionally, a control genomic DNA;
   (b) optionally, obtaining one or more reference values corresponding to the level of methylation at the genetic locus of SEQ ID NO: 11; and
   (c) identifying the sample as containing, or not containing, the blood cell based on the level of methylation at the genetic locus of SEQ ID NO: 11 in the genomic DNA isolated from the sample, the level of methylation at the genetic locus of SEQ ID NO: 11 in the genomic DNA obtained from the sample being determined by high-resolution melt (HRM) analysis, HRM comprising the steps of:
i) isolating the genomic DNA from the sample and optionally, the control sample;
ii) treating the isolated genomic DNA with bisulfite;
iii) polymerase chain reaction (PCR) amplifying the genetic locus of SEQ ID NO: 11 to produce the corresponding amplicon, the PCR amplifying being performed using a primer pair comprising SEQ ID NOs: 12 and 13; and
iv) determining the melting temperature of the amplicon; and
v) identifying the sample as containing, or not containing, the blood cell based on the melting temperature of the amplicon corresponding to the genetic locus of SEQ ID NO: 11 in the genomic DNA isolated from the sample.

2. The method of claim 1, wherein the control sample is obtained from a known blood cell or a cell other than the blood cell known to have methylation level at SEQ ID NO: 11 to be different from the methylation level at SEQ ID NO: 11 in the known blood cell.

3. The method of claim 1, wherein the cell other than the blood cell is a vaginal epithelial cell, a buccal cell, or a sperm.

4. The method of claim 1, wherein the sample is a forensic sample.

5. The method of claim 1, wherein the sample is processed to separate a cell suspected to be the blood cell before step (i) of isolating the genetic material.

6. A method for determining the level of methylation at the genetic locus of SEQ ID NO: 11 in a genomic DNA isolated from a cell, the method comprising the steps of:
i) isolating the genomic DNA from the cell;
ii) treating the isolated genomic DNA with bisulfite;
iii) PCR amplifying the genetic locus of SEQ ID NO: 11 to produce the corresponding amplicon, the PCR amplifying being performed using a primer pair comprising SEQ ID NOs: 12 and 13; and
iv) determining the melting temperature of the amplicon; and
v) identifying the level of methylation at the genetic locus of SEQ ID NO: 11 in the genomic DNA isolated from the cell based on the melting temperature of the amplicon produced in step iii).

7. The method of claim 6, wherein the cell is isolated from a forensic sample.

8. The method of claim 7, wherein the cell isolated from the forensic sample is suspected to be a blood cell.

9. A kit comprising a primer comprising SEQ ID NO: 12 and a primer comprising SEQ ID NO: 13.

10. The kit of claim 9, further comprising one or mere primer pairs selected from:
i) SEQ ID NOs: 2 and 3,
ii) SEQ ID NOs: 7 and 8, and
iii) SEQ ID NOs: 17 and 18.

* * * * *